United States Patent
Spencer et al.

(10) Patent No.: US 6,716,181 B2
(45) Date of Patent: Apr. 6, 2004

(54) FEMALE URINARY DEVICE

(75) Inventors: Dudley W. C. Spencer, Wilmington, DE (US); Ivars V. Ivansons, Wilmington, DE (US); Theresa M. Preston, Bear, DE (US)

(73) Assignee: Denco, Inc., Wilmington, DE (US)

( * ) Notice: Subject to any disclaimer, the term of this patent is extended or adjusted under 35 U.S.C. 154(b) by 140 days.

(21) Appl. No.: 10/155,477

(22) Filed: May 24, 2002

(65) Prior Publication Data

US 2003/0220586 A1 Nov. 27, 2003

(51) Int. Cl.⁷ .................................................. A61B 5/00
(52) U.S. Cl. .................................... 600/574; 604/329
(58) Field of Search ............................ 600/573, 574, 600/575, 29; 604/317, 327, 328, 329, 330, 331, 346, 347, 355

(56) References Cited

U.S. PATENT DOCUMENTS

| | | | | |
|---|---|---|---|---|
| 4,194,508 A | * | 3/1980 | Anderson | 604/329 |
| 4,904,248 A | * | 2/1990 | Vaillancourt | 604/329 |
| 5,049,144 A | * | 9/1991 | Payton | 604/329 |
| 5,053,027 A | * | 10/1991 | Manfredi | 604/327 |
| 5,263,947 A | * | 11/1993 | Kay | 604/331 |
| 5,295,983 A | * | 3/1994 | Kubo | 604/329 |
| 6,183,454 B1 | * | 2/2001 | Levine et al. | 604/329 |
| 6,342,049 B1 | * | 1/2002 | Nichols | 604/329 |
| 6,398,742 B1 | * | 6/2002 | Kim | 600/574 |
| 6,428,521 B1 | * | 8/2002 | Droll | 604/329 |

* cited by examiner

Primary Examiner—Charles Marmor
(74) Attorney, Agent, or Firm—Connolly Bove Lodge & Hutz

(57) ABSTRACT

A female urinary system includes an appliance which has a hollow urinary receiving open top body. The upper edge of the body is shaped to fit under the urethra. The body has an outlet passage for discharging urine flowing into the body from the urethra. A vaginal area locating bulb is mounted posteriorly of the body. The locating bulb has an arcuate outer surface having a contact portion which fits against the labia minora at the vestibule outwardly of the vagina. At least one longitudinal groove is provided on the posterior portion of the outer surface of the bulb from a location above the contact portion to the base of the bulb. A vent extends through the appliance from the hollow body below the upper edge to the base of the locating bulb.

21 Claims, 1 Drawing Sheet

FEMALE URINARY DEVICE

BACKGROUND OF THE INVENTION

For decades urinary incontinence or incontinency has been associated with shame, embarrassment and silence even though the World Health Organization estimates that there are 200 million worldwide with symptoms of male or female urinary incontinence. A true number is not known because the problem is so under reported. It is estimated that urinary incontinence affects 25 million Americans. This condition impacts quality of life by interfering with work, travel, social recreation and is associated with an increased number of falls, urinary tract infections and skin breakdown. Professionals are only recently learning progressive therapies for incontinence and many lay persons are still keeping their problem a secret. Prevention of this problem is a relatively new concept with little research data reported. Factors involved in bladder and/or sphincter problems and pelvic support are being looked at for preventing some forms of urinary incontinence.

Various devices have been disclosed in the patent literature attempting to address the problems of female urinary incontinence. For example, U.S. Pat. No. 3,335,714 discloses a device which concentrates on taking a sample of urine, but not a device intended for extended use. A portion of the "seal" area extends into a portion of the vagina for sealing purposes, but not for positioning purposes. A vent is not included in the device to enhance free-flow.

U.S. Pat. No. 3,512,185 discloses a device which covers both the vagina and the urethra areas with flexible shoulders to assist retention by the labia. The vagina is not used for positioning purposes.

U.S. Pat. No. 4,198,979 discloses a device using an adhesive to form a non-vented cavity that encompasses both the vagina and urethra. The device seal is designed to catch the body fluids of both the vagina and urethra. A portion of the seal enters the vagina to effect a complete adhesive seal. The device does not use the vagina for positioning or does not use a venting method. Entry into the vagina is for sealing only.

U.S. Pat. No. 4,496,355 discloses a device that collects urine via a sealing cup extending around the urethra and held in place by the labia. The seal area is "between" the vagina and the urethra. No mention is made of using the vagina for positioning purposes or venting the cavity that collects the urine.

U.S. Pat. No. 4,568,339 discloses a device using a groove into which an adhesive can be retained for "leak-free" fit around the urethra. The vagina cavity is not used.

U.S. Pat. No. 4,787,654 discloses a device which is designed to create a vacuum seal in a cup that surrounds the urethra. A vent is located in the line to allow urine to flow into the bag, but maintains a vacuum seal aided by the labia. The device makes no use of the vagina nor of a cup vent.

U.S. Pat. No. 4,795,449 discloses a form-fitting device using an adhesive surface for a leak-free cup. No mention is made of venting or of vagina positioning.

U.S. Pat. No. 4,846,819 discloses a device that uses a conformable gel to effect a complete "leak-free" seal around the urethra area. No mention is made of a vagina bulb or of a method of venting for free-flow of urine.

U.S. Pat. No. 4,904,248 discloses a device using an adhesive to effect a "leak-free" urethra cup that is vented in the tube area near the receptacle bag. The patent does not disclose the use of the vagina in any way, nor is the cup vented. Venting in the bag tubing will not effect free-flow from the device.

U.S. Pat. No. 6,342,049 discloses a device which is designed to use an "O" ring type of seal to effect a "leak-proof" seal around the urethra which does not include the vagina. A small lip on the sealing ring may be used to locate the seal by pressing on a portion of the vagina wall. No mention is made of venting the cup volume, because the device is designed for female astronauts.

SUMMARY OF THE INVENTION

A female urinary system includes an appliance, a portion of which is a hollow open top body having a peripheral rim for fitting under the urethra so that urine may flow into the body. The body has an outlet passage for discharging the urine into a collection bag. The appliance also includes a vaginal locating bulb extending posteriorly of the body. The bulb has an outer surface with a contact portion for fitting against the labia minora at the vestibule outwardly of the vagina. At least one longitudinal groove, and preferably a plurality of grooves, is provided on the posterior portion of the outer surface of the bulb. The grooves intersect the contact portion and extend downwardly for permitting the flow of fluid outwardly from the vagina when the locating bulb is mounted in place. Preferably, a vent extends from the hollow body through the appliance at the bulb to function as a vacuum break.

The portion of the bulb which is posterior of the hollow body is generally of oblong ball shape having a curved upper surface upwardly of the contact portion. The upper surface extends into the vestibule, but is spaced from the vagina. The hollow body is preferably in the shape of a discharge bowl which has a drain extension at its lower portion to function as the outlet passage. The interior of the bowl is tapered toward the extension so that the urine would flow into the extension. Preferably, the bulb and body are of one piece integral construction formed of a soft conformable material. A rim at the upper end of the body is preferably radially outwardly extending to permit the labia to fold around the rim at the seal area.

THE DRAWINGS

DETAILED DESCRIPTION

Figure 1:
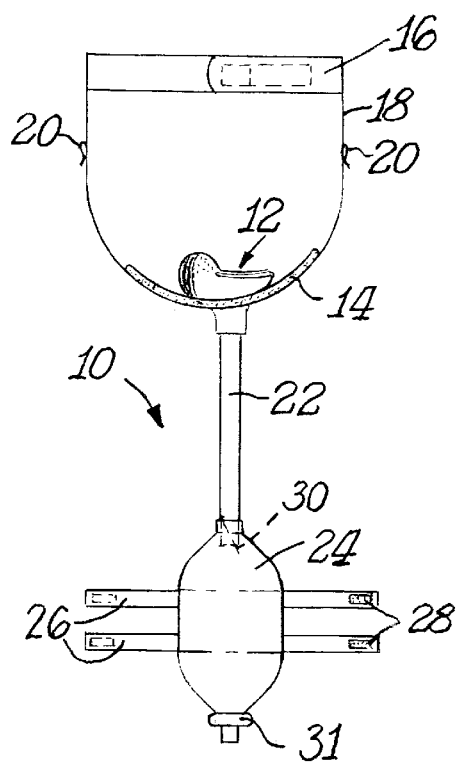
FIG. 1 is a side elevational view of a female urinary system in accordance with this invention.

FIG. 1 illustrates a female urinary system 10 of this invention. As shown therein system 10 includes an appliance 12 which is shown in greater detail in FIGS. 2–4. Appliance 12 may be disposed against, for example, a conventional sanitary napkin 14 which in turn is mounted to an adjustable waist belt 16 by any suitable means such as by support band 18 having gauze fasteners 20. A drain tube 22 is mounted to the lower end of appliance 12 to convey urine into any suitable receptacle such as a leg bag 24 which would be mounted to the leg of the wearer by any suitable means. FIG. 1, for example, illustrates straps 26 having velcro (hook and loop) formations 28. Flow of the urine from drain tube 22 into leg bag 24 may be controlled in any suitable manner such as by a reed valve 30.

Periodically or when a sufficient amount of urine has been collected in the collection bag 24, the bag 24 can be completely replaced by closing the drain tube valve 30 and then removing the old bag and reattaching a new bag whereupon the reed valve 30 would again be opened. Alternatively, the bag could be emptied by opening the drain valve 31 at the bottom of the bag.

Figure 3:
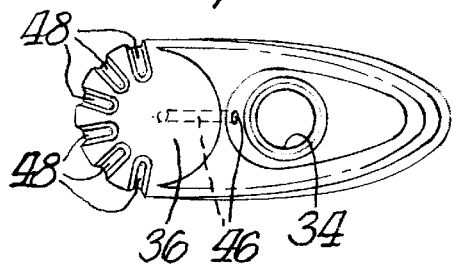
FIG. 3 is a top plan view of the appliance shown in FIG. 2.
Figure 2:
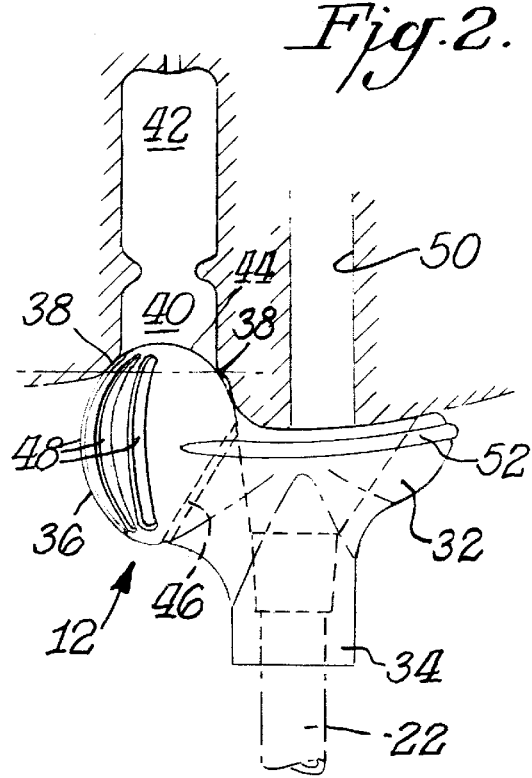
FIG. 2 is a side elevational view schematically showing the appliance of the system of FIG. 1 mounted in place.
Figure 4:
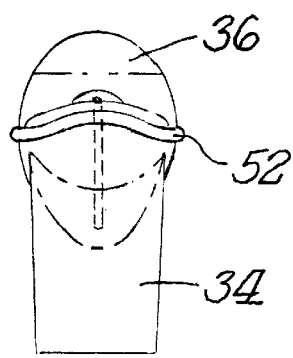
FIG. 4 is a right end elevational view of the appliance shown in FIGS. 2–3.

FIG. 2 best shows the manner of mounting the appliance 12. As shown therein appliance 12 includes an open top hollow body 32 having a tubular downward extension 34 into which the drain tube 22 is mounted. As shown in FIG. 3 the hollow body has an upper top and functions as a discharge bowl which is generally egg-shaped having a narrow end and a wide end. The drainage extension 34 is located at the wide end. A vaginal locating bulb 36 is mounted posteriorly of body 32. Preferably body 32 and locating bulb 36 are of one piece integral construction formed of any suitable material. A preferred material would be a silicon or silastics material which is approved by the FDA for this type of application. Such material is soft and conforms to the body for a comfortable and flexible fit.

The locating bulb 36 in its posterior portion outwardly of body 32 may be formed of any suitable shape to achieve its intended purposes. In the preferred illustrated form locating bulb 36 has an oblong ball shape so that it is of arcuate outer surface throughout its shape which avoids sharp edges that might cause irritation. The invention, however, may be practiced with other shapes, such as by having portions flat and non-arcuate.

As shown in FIG. 2 the vaginal locating bulb 36 is mounted against the labia minora 38 at the vestibule 40 outwardly of the vagina 42. Thus the arcuate portion or protuberance 44 at the upper end of locating bulb 36 extends slightly into the vestibule outwardly from the contact portion of the outer surface of locating bulb 36 with the labia minora 38. Significantly, however, the bulb does not extend into the vagina. Instead, the bulb is located at least one centimeter away from the vagina. As a result, this avoids the possibility of toxic shock syndrome which might otherwise occur if the bulb were extended into the vagina. In addition, by locating the bulb outwardly of the vagina there is avoidance of any scratching of the vaginal wall which might otherwise cause cervical cancer. This is a distinct advantage over such prior art as the device disclosed in U.S. Pat. No. 6,342,049 which refers to the device being within the vagina by means of engagement of the vaginal walls and the anchoring member supported within the vaginal cavity. Accordingly, locating bulb 36 is not a pessary such as a tampon (which is known to cause toxic shock syndrome) and is not a balloon (which is known to cause cervical wall scratching, a precursor to cervical cancer). Instead, locating bulb 36 is designed to make minimal contact with the labium minus (labia minora) tissue at the vestibule which is well below the hymen cusp and approximately 1 cm below the vaginal walls. In this way the known dangers of pessary devices are avoided. In addition, by including a vent passage 46 (as later described), the urethra cup is vented to prevent creating a vacuum seal.

As best shown in FIGS. 2–3 a plurality and preferably six longitudinal grooves 48 extend downwardly from above the labia minora contact portion of the outer surface of locating bulb 36 toward the base of the bulb. These longitudinal grooves 48 in the posterior area of the locating bulb 36 provide for free flow and discharge of vaginal mucus and menses. The invention could be practiced with a lesser or greater number of grooves. At least one groove is included to provide a passage for flow of fluid from the vagina. A plurality of grooves, however, is particularly preferred to assure that such flow will be permitted.

The body portion 32 of appliance 12 is located below the urethra 50 as schematically shown in FIG. 2. Body 32 is a discharge bowl of open or hollow construction having a tapered inner wall which tapers downwardly toward tube-like hollow extension 34 so that extension 34 can function as an outlet passage for urine flowing from the urethra into body or collection device 32. Preferably, a rib 52 in the form of a supplementary ring is molded near the top of the main seal surface of body 32 to aid in retention of the appliance 12 via the labia whereby the labia is permitted to fold around the rib 52.

As previously indicated a vent passage 46 extends through appliance 12. The upper end of vent 46 is located at the body 32 in the wall which is common to bulb 36, slightly below the upper end of the wall. See FIG. 4. The lower end of vent 46 is located at the base of bulb 36. The vent 46 thus extends completely through the appliance 12 from the outside to the inside of the urine collection sealed cavity and functions as a vacuum break. As a result, the vent 46 allows rapid and free flow of urine from the body 32. This would be analogous to the action of breaking a vacuum that one can create of retaining fluid in a soda straw. By closing the tube top with one's finger, flow will stop.

The appliance 12 has a number of distinct advantageous characteristics. For example, the vaginal locating bulb 36 makes the appliance location and placement safe, accurate and comfortable. Although the locating bulb 36 gives slight anchoring, its primary function is as a locating device. By molding the bulb 36 (which protects the vaginal orifice) into the urethra covering, the appliance 12 prevents *E-Coli* and other pathogens from the anus discharge from creating urinary tract infections.

By changing the materials of construction and the price of a kit incorporating the components of the system 10 it is possible to have different models available, such as models that could be usable for 10 hours or 100 hours or 1,000 hours. The short time use would be for a system that is disposable after a single use. Such use could be non-postoperative. The device for intermediate time use could be disposable after use, but could be used in postoperative hospital conditions. The long term version could be for chronic use and could be reusable. Such use for acute and chronic incontinence and for postoperative urinary drainage eliminates the danger of urinary tract infection. The system 10 is discreet, unobtrusive and comfortable. When used with a sanitary napkin the sanitary napkin could function for menses and/or other discharges. The appliance 12 does not interfere with periods or with anal discharges while the appliance is mounted in place thereby avoiding accidental urinary tract contaminants. The system 10 can be used intermittently for activities such as social, travel or continuous use with urinary tract infection therapy or chronic incontinence. Thus, the system 10 could be used for short periods of time or as a semi-permanent device that can be used for extended periods of time (months) with the ability to be removed and replaced easily for sanitary cleaning purposes (daily). Since urine is a sterile fluid the system is regularly flushed thus avoiding sepsis when in use. If a catheter is needed for acute bladder voiding the device 10 can be used in place to accurately locate the urethral distal entrance point. The collection receptacle, such as bag 24 can have its contents drained at will by an aseptic hand operated urine exit valve 31. The system 10 provides an extremely comfortable device when in use and is effective from upright, sitting or supine positions.

What is claimed is:

1. A female urinary system comprising an appliance, said appliance being a hollow open top urine receiving body, said body having an upper edge for fitting under the urethra whereby urine may flow into said body, said body having an outlet passage for discharging the urine flowing into said body, a vaginal locating bulb extending posteriorly of said body, said locating bulb having an outer surface, said outer surface including a contact portion for fitting against the labia minora at the vestibule outwardly of the vagina, and at least one longitudinal groove on the posterior portion of said outer surface of said locating bulb intersecting said contact portion and extending downwardly therefrom for permitting the flow of fluid to flow outwardly from the vagina when said locating bulb is mounted in place.

2. The system of claim 1 including a vent extending through said appliance from said hollow body to function as a vacuum break.

3. The system of claim 2 wherein said vent extends from said hollow body to the base of said locating bulb.

4. The system of claim 1 wherein there are a plurality of said longitudinal grooves.

5. The system of claim 4 wherein said locating bulb has an arcuate surface upwardly from said contact portion for extending slightly into the vestibule but spaced from the vagina.

6. The system of claim 5 wherein said locating bulb posteriorly of said body is of oblong ball shape with said outer surface being completely arcuate.

7. The system of claim 6 wherein said grooves are confined to the posterior portion of said outer surface and extend from above said contact portion of said locating bulb to the base of said locating bulb.

8. The system of claim 1 wherein said body is in the form of a discharge bowl, said outlet passage being a drain extension communicating with said discharge bowl, and said discharge bowl having a tapered inner wall which tapers downwardly toward said extension.

9. The system of claim 1 wherein said locating bulb and said body are integrally molded of one-piece construction.

10. The system of claim 1 wherein a radially extending rib is located outwardly of said body below said upper edge for providing a location over which the labia may fold.

11. The system of claim 1 wherein a drain tube is mounted in said outlet passage for conveying the urine away from said body, said drain tube communicating with a collection bag, fasteners on said bag for mounting said bag to the user, a sanitary napkin, said appliance being disposed on said sanitary napkin, a belt for being mounted on the user, and said sanitary napkin being secured to said belt.

12. A female urinary system comprising an appliance, said appliance being a hollow open top urine receiving body, said body having an upper edge for fitting under the urethra whereby urine may flow into said body, said body having an outlet passage for discharging the urine flowing into said body, a vaginal locating bulb extending posteriorly of said body, said locating bulb having an outer surface, said outer surface including a contact portion for fitting against the labia minora at the vestibule outwardly of the vagina, and a vent extending through said appliance from said body to function as a vacuum break, wherein said vent extends from a location below said upper edge of said body to the base of said locating bulb.

13. The system of claim 12 wherein one end of said vent is located in said body at a wall common to said bulb.

14. The system of claim 12 wherein said locating bulb has an arcuate surface upwardly from said contact portion for extending slightly into the vestibule.

15. The system of claim 12 wherein said body is in the form of a discharge bowl, said outlet passage being a drain extension communicating with said discharge bowl, and said discharge bowl having a tapered inner wall which tapers downwardly toward said extension.

16. The system of claim 12 wherein said locating bulb and said body are integrally molded of one-piece construction.

17. The system of claim 12 wherein a radially extending rib is located outwardly of said body below said upper edge for providing a location over which the labia may fold.

18. The system of claim 13 wherein said locating bulb posteriorly of said body is of oblong ball shape with said outer surface being completely arcuate.

19. The system of claim 12 wherein a drain tube is mounted in said outlet passage for conveying the urine away from said body, said drain tube communicating with a collection bag, fasteners on said bag for mounting said bag to the user, a sanitary napkin, said appliance being disposed on said sanitary napkin, a belt for being mounted on the user, and said sanitary napkin being secured to said belt.

20. A method of collecting urine from a female user comprising providing an appliance having a hollow open top urine receiving body with a posteriorly extending vaginal locating bulb mounted to the body, disposing the locating bulb against the labia minora at the vestibule outwardly of the vagina, disposing the upper edge of the hollow open top body under the urethra, folding the labia over an outwardly extending rib on the body, providing at least one longitudinal groove on the outer surface of the locating bulb extending from above a contact portion of the bulb with the labia minora to the base of the bulb, and permitting the urine to flow from the urethra into the body and to pass from the body through an outlet passage in the body to be collected in a collection container.

21. The method of claim 20 including providing a vent which extends through the appliance from a location within the body below the upper edge to the base of the locating bulb, and utilizing the vent as a vacuum break.

* * * * *